United States Patent
Lim et al.

(10) Patent No.: US 10,236,532 B2
(45) Date of Patent: Mar. 19, 2019

(54) ADDITIVE FOR ELECTROLYTE AND ELECTROLYTE AND RECHARGEABLE LITHIUM BATTERY

(71) Applicant: Samsung SDI Co., Ltd., Yongin-si, Gyeonggi-do (KR)

(72) Inventors: Jin-Hyeok Lim, Yongin-si (KR); Ho-Seok Yang, Yongin-si (KR); Yun-Hee Kim, Yongin-si (KR); Young Sam Park, Yongin-si (KR); Hee-Yeon Hwang, Yongin-si (KR); Hyun-Woo Kim, Yongin-si (KR)

(73) Assignee: Samsung SDI Co., Ltd., Gyeonggi-do (KR)

( * ) Notice: Subject to any disclaimer, the term of this patent is extended or adjusted under 35 U.S.C. 154(b) by 385 days.

(21) Appl. No.: 14/616,598

(22) Filed: Feb. 6, 2015

(65) Prior Publication Data

US 2015/0229003 A1 Aug. 13, 2015

(30) Foreign Application Priority Data

Feb. 10, 2014 (KR) ........................ 10-2014-0014936

(51) Int. Cl.
*H01M 10/0567* (2010.01)
*H01M 10/052* (2010.01)
*C07D 207/327* (2006.01)

(52) U.S. Cl.
CPC .... *H01M 10/0567* (2013.01); *C07D 207/327* (2013.01); *H01M 10/052* (2013.01); *H01M 2300/0025* (2013.01)

(58) Field of Classification Search
CPC .......... H01M 10/0567; H01M 10/052; H01M 2300/0025
See application file for complete search history.

(56) References Cited

U.S. PATENT DOCUMENTS 5,759,714 A * 6/1998 Matsufuji ............. H01M 4/485
429/218.1
6,593,487 B1 7/2003 Starner et al.
(Continued)

FOREIGN PATENT DOCUMENTS

KR 10-2000-0072955 A 12/2000
KR 10-2003-0051337 A 6/2003
(Continued)

*Primary Examiner* — Osei K Amponsah
(74) *Attorney, Agent, or Firm* — Knobbe, Martens, Olson & Bear LLP

(57) ABSTRACT

Disclosed are an additive for an electrolyte represented by the following Chemical Formula 1, and an electrolyte and a rechargeable lithium battery including the same:

[Chemical Formula 1]

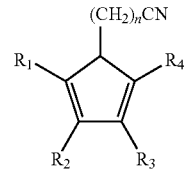

wherein $R_1$ to $R_4$ and n are the same as described in the detailed description.

12 Claims, 6 Drawing Sheets

(56) References Cited

U.S. PATENT DOCUMENTS

2012/0077076 A1* 3/2012 Cheng ............... H01M 10/0525
429/156
2012/0251895 A1* 10/2012 Mun ................. H01M 10/0567
429/338
2012/0258349 A1 10/2012 Hayakawa et al.

FOREIGN PATENT DOCUMENTS

KR 10-2012-0105338 A 9/2012
KR 10-2012-0114170 A 10/2012

* cited by examiner

ADDITIVE FOR ELECTROLYTE AND ELECTROLYTE AND RECHARGEABLE LITHIUM BATTERY

CROSS-REFERENCE TO RELATED APPLICATIONS

This application claims priority to and the benefit of Korean Patent Application No. 10-2014-0014936 filed in the Korean Intellectual Property Office on Feb. 10, 2014, the entire contents of which are incorporated herein by reference.

BACKGROUND

Field

An additive for an electrolyte, and an electrolyte and a rechargeable lithium battery including the same are disclosed.

Description of the Related Art

A battery converts chemical energy generated from an electrochemical redox reaction of a chemical material in the battery into electrical energy. Such a battery is divided into a primary battery, which should be disposed after the energy of the battery is all consumed, and a rechargeable battery, which may be recharged many times. The rechargeable battery may be charged/discharged many times based on the reversible conversion between chemical energy and electrical energy.

Recent developments in high-tech electronics have allowed electronic devices to become small and light in weight, which leads to an increase in portable electronic devices. As a power source for such portable electronic devices, the demands for batteries with high energy density are increasing and researches on lithium rechargeable battery are briskly under progress.

The rechargeable lithium battery is manufactured by an injecting electrolyte into an electrode assembly, which includes a positive electrode including a positive active material capable of intercalating/deintercalating lithium and a negative electrode including a negative active material capable of intercalating/deintercalating lithium.

An electrolyte includes an organic solvent in which a lithium salt is dissolved and critically determines stability and performance of a rechargeable lithium battery.

SUMMARY

One embodiment provides an additive for an electrolyte being capable of improving performance while ensuring stability at a high voltage.

Another embodiment provides an electrolyte for a rechargeable lithium battery including the additive for an electrolyte.

Yet another embodiment provides a rechargeable lithium battery including the electrolyte.

According to one embodiment, an additive for an electrolyte represented by the following Chemical Formula 1 provided.

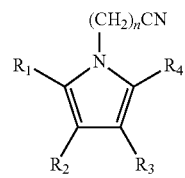

[Chemical Formula 1]

In the above Chemical Formula 1, $R^1$ to $R^4$ are independently at least one selected from a hydrogen atom, a substituted or unsubstituted C1 to C12 alkyl group, a substituted or unsubstituted C2 to C12 alkenyl group, a substituted or unsubstituted C2 to C12 alkynyl group, a C1 to C12 alkoxy group, a substituted or unsubstituted C3 to C12 cycloalkyl group, a substituted or unsubstituted C3 to C12 cycloalkenyl group, a substituted or unsubstituted C3 to C12 cycloalkynyl group, a substituted or unsubstituted C2 to C12 heterocycloalkyl group, a substituted or unsubstituted C2 to C12 heterocycloalkenyl group, a substituted or unsubstituted C2 to C12 heterocycloalkynyl group, a substituted or unsubstituted C6 to C20 aryloxy group, a halogen atom, a substituted or unsubstituted C1 to C12 fluoroalkyl group, a nitro group, a substituted or unsubstituted C6 to C20 aryl group, a substituted or unsubstituted C2 to C20 heteroaryl group, a substituted or unsubstituted C6 to C20 haloaryl group, $-NR^5R^6$ ($R^5$ and $R^6$ are independently at least one selected from an alkyl group, an alkenyl group, an aryl group, and an oxaalkyl group, or $R^5$ and $R^6$ may form a ring), $R^7-C(O)-$, $R^7-O-C(O)-$, $R^7-C(O)-O-$, $R^7-O-C(O)-CH_2-$ ($R^7$ is at least one selected from an alkyl group, an aryl group, a fluoroalkyl group, a haloaryl group, and a heteroaryl group) $-OR'$ ($R'$ is a C1 to C12 alkyl group) and $-R''C(O)-OR'''$ ($R''$ is a C1 to C4 alkyl group, and $R'''$ is a C1 to C12 alkyl group), and n is an integer ranging from 1 to 3.

For example, the above Chemical Formula 1 may be represented by the following Chemical Formula 2.

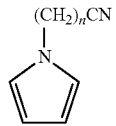

[Chemical Formula 2]

In the above Chemical Formula 2,
n is an integer ranging from 1 to 3.
For example, the above Chemical Formula 1 may be represented by the following Chemical Formula 3.

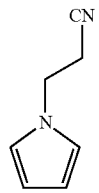

[Chemical Formula 3]

According to another embodiment, provided is an electrolyte for a rechargeable lithium battery including a lithium salt, a non-aqueous organic solvent and the additive for an electrolyte represented by the above Chemical Formula 1.

The additive for an electrolyte may be represented by the above Chemical Formula 2 or Chemical Formula 3.

The additive for an electrolyte may be included in an amount of about 0.001 parts by weight to about 1 part by weight based on 100 parts by weight of the non-aqueous organic solvent.

According to yet another embodiment, provided is a rechargeable lithium battery including a positive electrode including a positive active material, a negative electrode including a negative active material and the electrolyte.

The rechargeable lithium battery may further include a passivation film disposed on the surface of the positive electrode.

The rechargeable lithium battery may be operated at a voltage region of greater than or equal to about 4.35 V.

The additive for an electrolyte may form a stable passivation film on the surface of the positive electrode and thus improve battery performance.

DETAILED DESCRIPTION OF THE PREFERRED EMBODIMENT

Figure 1:
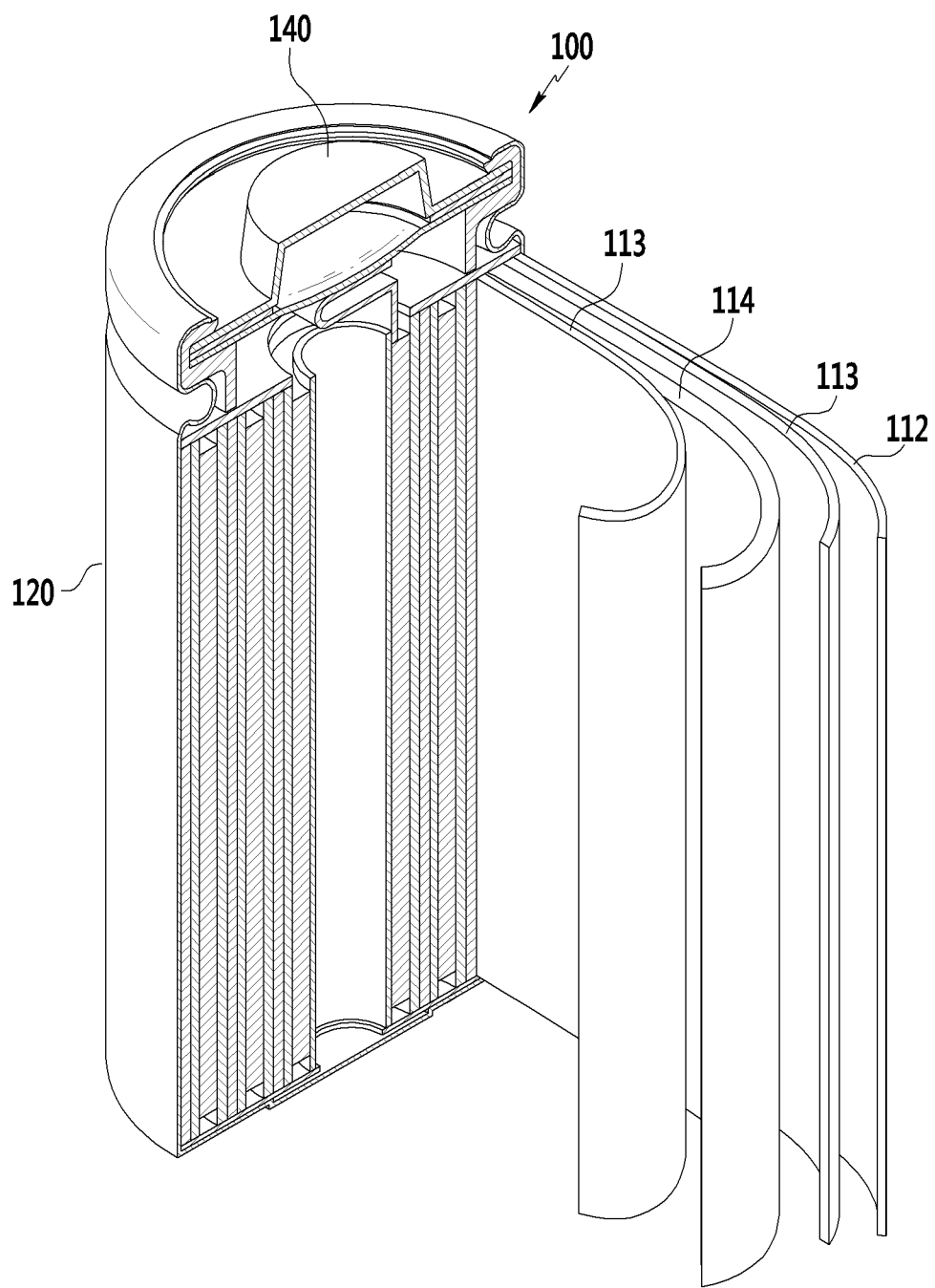
FIG. 1 is a schematic view showing a rechargeable lithium battery according to one embodiment.

Example embodiments will hereinafter be described in detail, and may be easily performed by those who have common knowledge in the related art. However, this disclosure may be embodied in many different forms and is not construed as limited to the example embodiments set forth herein.

As used herein, when a definition is not otherwise provided, the term "substituted" refers to one substituted with a halogen atom (F, Cl, Br or I), a hydroxy group, an alkoxy group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, a phosphoric acid or a salt thereof, a C1 to C20 alkyl group, a C2 to C20 alkenyl group, a C2 to C20 alkynyl group, a C6 to C30 aryl group, a C7 to C30 arylalkyl group, a C1 to C20 alkoxy group, a C1 to C20 heteroalkyl group, a C3 to C20 heteroarylalkyl group, a C3 to C30 cycloalkyl group, a C3 to C15 cycloalkenyl group, a C6 to C15 cycloalkynyl group, a C2 to C20 heterocycloalkyl group, and a combination thereof, instead of at least one hydrogen of a compound.

As used herein, when a definition is not otherwise provided, the term 'hetero' refers to one including 1 to 3 heteroatoms selected from N, O, S, and P.

Hereinafter, an additive for an electrolyte according to one embodiment is described.

An additive for an electrolyte according to one embodiment is a compound represented by the following Chemical Formula 1.

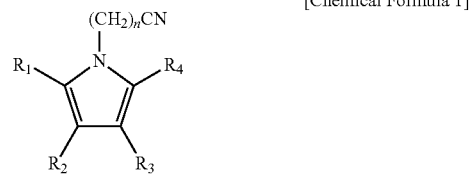

[Chemical Formula 1]

In the above Chemical Formula 1, $R_1$ to $R_4$ are independently a hydrogen atom, a substituted or unsubstituted C1 to C12 alkyl group, a substituted or unsubstituted C2 to C12 alkenyl group, a substituted or unsubstituted C2 to C12 alkynyl group, a C1 to C12 alkoxy group, a substituted or unsubstituted C3 to C12 cycloalkyl group, a substituted or unsubstituted C3 to C12 cycloalkenyl group, a substituted or unsubstituted C3 to C12 cycloalkynyl group, a substituted or unsubstituted C2 to C12 heterocycloalkyl group, a substituted or unsubstituted C2 to C12 heterocycloalkenyl group, a substituted or unsubstituted C2 to C12 heterocycloalkynyl group, a substituted or unsubstituted C6 to C20 aryloxy group, a halogen atom, a substituted or unsubstituted C1 to C12 fluoroalkyl group, a nitro group, a substituted or unsubstituted C6 to C20 aryl group, a substituted or unsubstituted C2 to C20 heteroaryl group, a substituted or unsubstituted C6 to C20 haloaryl group, —$NR^5R^6$ ($R^5$ and $R^6$ are independently at least one selected from an alkyl group, an alkenyl group, an aryl group, and an oxaalkyl group, or $R^5$ and $R^6$ may be fused to each other to form a ring), $R^7$—C(O)—, $R^7$—O—C(O)—, $R^7$—C(O)—O—, $R^7$—O—C(O)—$CH_2$— ($R^7$ is at least one selected from an alkyl group, an aryl group, a fluoroalkyl group, a haloaryl group, and a heteroaryl group), —OR' (R' is a C1 to C12 alkyl group) and —R"C(O)—OR'" (R" is a C1 to C4 alkyl group, and R'" is a C1 to C12 alkyl group), and n is an integer ranging from 1 to 3.

Specifically, the additive for an electrolyte may be, for example a compound represented by the following Chemical Formula 2.

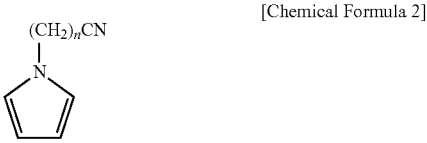

[Chemical Formula 2]

In the above Chemical Formula 2, n is an integer ranging from 1 to 3.

In some embodiments, the additive for an electrolyte may be a compound represented by the following Chemical Formula 3.

[Chemical Formula 3]

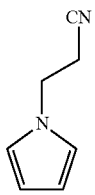

The additive for an electrolyte may be added to an electrolyte for a rechargeable lithium battery. The additive for an electrolyte may increase stability by improving flame retardancy of the electrolyte and cause a decomposition reaction on the surface of a positive electrode and form a stable passivation film, thereby improving cycle-life characteristics of a battery.

Hereinafter, an electrolyte for a rechargeable lithium battery according to one embodiment is described.

An electrolyte for a rechargeable lithium battery according to one embodiment includes a lithium salt, a non-aqueous organic solvent, and an additive.

The lithium salt is dissolved in an organic solvent, supplies lithium ions in a battery, operates a basic operation of the rechargeable lithium battery, and improves lithium ion transportation between positive and negative electrodes therein. Examples of the lithium salt may be one or more of $LiPF_6$, $LiBF_4$, $LiSbF_6$, $LiAsF_6$, $LiN(SO_2C_2F_5)_2$, $Li(CF_3SO_2)_2N$, $LiN(SO_3C_2F_5)_2$, $LiCF_3SO_3$, $LiC_4F_9SO_3$, $LiClO_4$, $LiAlO_2$, $LiAlCl_4$, $LiC(CF_3SO_2)_3$, $LiN(C_xF_{2x+1}SO_2)(C_yF_{2y+1}SO_2)$, wherein x and y are natural numbers, e.g., an integer of 1 to 20, LiCl, and LiI.

The lithium salt may be used in a concentration of from about 0.1 M to about 2.0 M. When the lithium salt is included at the above concentration range, an electrolyte may have excellent performance and lithium ion mobility due to optimal electrolyte conductivity and viscosity.

The non-aqueous organic solvent serves as a medium for transmitting ions taking part in the electrochemical reaction of a battery.

The non-aqueous organic solvent may be selected from a carbonate-based, ester-based, ether-based, ketone-based, alcohol-based, or aprotic solvent. The carbonate-based solvent includes dimethyl carbonate (DMC), diethyl carbonate (DEC), dipropyl carbonate (DPC), methylpropyl carbonate (MPC), ethylpropyl carbonate (EPC), ethylmethyl carbonate (EMC), ethylene carbonate (EC), fluoroethylene carbonate (FEC), propylene carbonate (PC), butylene carbonate (BC), and the like, and the ester-based solvent includes methyl acetate, ethyl acetate, n-propyl acetate, dimethylacetate, methyl propionate, ethyl propionate, ethyl butyrate, gamma-butyrolactone, decanolide, gamma-valerolactone, mevalonolactone, caprolactone, and the like.

The ether-based solvent includes dibutyl ether, tetraglyme, diglyme, dimethoxyethane, 2-methyltetrahydrofuran, tetrahydrofuran, and the like, and the ketone-based solvent includes cyclohexanone, and the like. In addition, the alcohol-based solvent may be ethanol, isopropyl alcohol, and the like. The aprotic solvent may include nitriles such as R—CN (R is a hydrocarbon group having a C2 to C20 linear, branched, or cyclic structure, and may include a double bond, an aromatic ring, or an ether bond) and the like, amides such as dimethyl formamide and the like, dioxolanes such as 1,3-dioxolane and the like, sulfolanes, and the like.

The non-aqueous organic solvent may be used singularly or in a mixture. When the organic solvent is used in a mixture, the mixture ratio may be controlled in accordance with a desirable battery performance.

The carbonate-based solvent is prepared by mixing a cyclic carbonate and a linear carbonate. The cyclic carbonate and the linear carbonate are mixed together in the volume ratio of about 1:1 to about 1:9. Within this range, performance of electrolyte may be improved.

The non-aqueous organic solvent of the present embodiments includes an aromatic hydrocarbon-based organic solvent as well as the carbonate based solvent. The carbonate-based and the aromatic hydrocarbon-based solvents may be mixed together in a volume ratio ranging from about 1:1 to about 30:1.

Specific examples of the aromatic hydrocarbon-based organic solvent may be selected from benzene, fluorobenzene, 1,2-difluorobenzene, 1,3-difluorobenzene, 1,4-difluorobenzene, 1,2,3-trifluorobenzene, 1,2,4-trifluorobenzene, chlorobenzene, 1,2-dichlorobenzene, 1,3-dichlorobenzene, 1,4-dichlorobenzene, 1,2,3-trichlorobenzene, 1,2,4-trichlorobenzene, iodobenzene, 1,2-diiodobenzene, 1,3-diiodobenzene, 1,4-diiodobenzene, 1,2,3-triiodobenzene, 1,2,4-triiodobenzene, toluene, fluorotoluene, 2,3-difluorotoluene, 2,4-difluorotoluene, 2,5-difluorotoluene, 2,3,4-trifluorotoluene, 2,3,5-trifluorotoluene, chlorotoluene, 2,3-dichlorotoluene, 2,4-dichlorotoluene, 2,5-dichlorotoluene, 2,3,4-trichlorotoluene, 2,3,5-trichlorotoluene, iodotoluene, 2,3-diiodotoluene, 2,4-diiodotoluene, 2,5-diiodotoluene, 2,3,4-triiodotoluene, 2,3,5-triiodotoluene, xylene, and a combination thereof.

The additive may be represented by the following Chemical Formula 1.

[Chemical Formula 1]

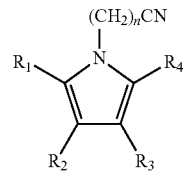

In the above Chemical Formula 1, $R_1$ to $R_4$ are independently at least one selected from a hydrogen atom, a substituted or unsubstituted C1 to C12 alkyl group, a substituted or unsubstituted C2 to C12 alkenyl group, a substituted or unsubstituted C2 to C12 alkynyl group, a C1 to C12 alkoxy group, a substituted or unsubstituted C3 to C12 cycloalkyl group, a substituted or unsubstituted C3 to C12 cycloalkenyl group, a substituted or unsubstituted C3 to C12 cycloalkynyl group, a substituted or unsubstituted C2 to C12 heterocycloalkyl group, a substituted or unsubstituted C2 to C12 heterocycloalkenyl group, a substituted or unsubstituted C2 to C12 heterocycloalkynyl group, a substituted or unsubstituted C6 to C20 aryloxy group, a halogen atom, a substituted or unsubstituted C1 to C12 fluoroalkyl group, a nitro group, a substituted or unsubstituted C6 to C20 aryl group, a substituted or unsubstituted C2 to C20 heteroaryl group, a substituted or unsubstituted C6 to C20 haloaryl group, —$NR^5R^6$ ($R^5$ and $R^6$ are independently at least one selected from an alkyl group, an alkenyl group, an aryl group, and an oxaalkyl group, or $R^5$ and $R^6$ may be fused to each other to form a ring) $R^7$—C(O)—, $R^7$—O—C(O)—, $R^7$—C(O)—O—, $R^7$—O—C(O)—$CH_2$— ($R^7$ is at least one selected from an alkyl group, an aryl group, a fluoroalkyl group, a haloaryl group, and a heteroaryl group), —OR' (R' is a C1 to C12 alkyl group) and —R"C(O)—OR'" (R" is a C1 to C4 alkyl group, and R'" is a C1 to C12 alkyl group), and n is an integer ranging from 1 to 3.

The additive may be, for example a compound represented by the following Chemical Formula 2 or Chemical Formula 3.

[Chemical Formula 2]

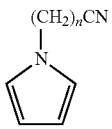

In the above Chemical Formula 2,
n is an integer ranging from 1 to 3.

[Chemical Formula 3]

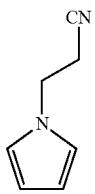

The additive for an electrolyte may increase stability by improving flame retardancy of the electrolyte and cause a decomposition reaction on the surface of a positive electrode and form a stable passivation film, thereby improving cycle-life characteristics of a battery.

The additive for an electrolyte may be included in an amount of about 0.001 parts by weight to about 1 part by weight based on 100 parts by weight of the non-aqueous organic solvent. The additive included within the range may effectively improve flame retardancy and also, be decomposed on the surface of an electrode and thus, form a stable passivation film.

Hereinafter, a rechargeable lithium battery according to another embodiment is described referring to a drawing.

FIG. 1 is a schematic view of a rechargeable lithium battery according to one embodiment.

Referring to FIG. 1, a rechargeable lithium battery 100 according to one embodiment includes an electrode assembly including a negative electrode 112, a positive electrode 114 facing the negative electrode 112, a separator 113 interposed between the negative electrode 112 and the positive electrode 114, and an electrolyte (not shown) impregnating the negative electrode 112, the positive electrode 114, and the separator 113, a battery case 120 housing the battery cell, and a sealing member 140 sealing the battery case 120.

The rechargeable lithium battery 100 is manufactured by sequentially stacking the negative electrode 112, separator 113, and positive electrode 114 and spiral-winding them and housing the wound resultant in the battery case 120.

The negative electrode 112 includes a current collector and a negative active material layer formed on the current collector.

The current collector may be a copper foil, a nickel foil, a stainless steel foil, a titanium foil, a nickel foam, a copper foam, a polymer substrate coated with a conductive metal, or a combination thereof.

The negative active material layer includes a negative active material, a binder, and optionally a conductive material.

The negative active material includes a material that reversibly intercalates/deintercalates lithium ions, a lithium metal, a lithium metal alloy, material being capable of doping and dedoping lithium, or a transition metal oxide.

The material that reversibly intercalates/deintercalates lithium ions is a carbon material, and may be any generally-used carbon-based negative active material in a rechargeable lithium ion battery, and examples thereof may be crystalline carbon, amorphous carbon, or a combination thereof. Examples of the crystalline carbon may be a graphite such as a shapeless, sheet-shaped, flake, spherical shaped or fiber-shaped natural graphite or artificial graphite, and examples of the amorphous carbon may be soft carbon or hard carbon, a mesophase pitch carbonized product, fired cokes, and the like.

The lithium metal alloy may include an alloy of lithium and a metal of Na, K, Rb, Cs, Fr, Be, Mg, Ca, Sr, Si, Sb, Pb, In, Zn, Ba, Ra, Ge, Al, or Sn.

The material being capable of doping and dedoping lithium may be Si, $SiO_x$ (0<x<2), a Si—C composite, a Si-Q alloy (wherein Q is an alkali metal, an alkaline-earth metal, Group 13 to 16 elements, a transition metal, a rare earth element, or a combination thereof, and not Si), Sn, $SnO_2$, a Sn—C composite, Sn—$R^8$ (wherein R is an alkali metal, an alkaline-earth metal, Group 13 to 16 elements, a transition metal, a rare earth element, or a combination thereof, and not Sn), and the like. Specific examples of the Q and $R^8$ may be Mg, Ca, Sr, Ba, Ra, Sc, Y, Ti, Zr, Hf, Rf, V, Nb, Ta, Db, Cr, Mo, W, Sg, Tc, Re, Bh, Fe, Pb, Ru, Os, Hs, Rh, Ir, Pd, Pt, Cu, Ag, Au, Zn, Cd, B, Al, Ga, Sn, In, Tl, Ge, P, As, Sb, Bi, S, Se, Te, Po, or a combination thereof.

The transition metal oxide may be vanadium oxide, lithium vanadium oxide, and the like.

The binder improves binding properties of negative active material particles with one another and with a current collector. The binder includes a non-water-soluble binder, a water-soluble binder, or a combination thereof.

In some embodiments, the non-water-soluble binder includes polyvinylchloride, carboxylated polyvinylchloride, polyvinylfluoride, an ethylene oxide-containing polymer, polyvinylpyrrolidone, polyurethane, polytetrafluoroethylene, polyvinylidene fluoride, polyethylene, polypropylene, polyamideimide, polyimide, or a combination thereof.

In some embodiments, the water-soluble binder includes a styrene-butadiene rubber, an acrylated styrene-butadiene rubber, polyvinyl alcohol, sodium polyacrylate, a copolymer of propylene and a C2 to C8 olefin, a copolymer of (meth) acrylic acid and (meth)acrylic acid alkyl ester, or a combination thereof.

When the water-soluble binder is used as a negative electrode binder, a cellulose-based compound may be further used to provide viscosity. In some embodiments, the cellulose-based compound includes one or more of carboxylmethyl cellulose, hydroxypropylmethyl cellulose, methyl cellulose, or alkali metal salts thereof. In some embodiments, the alkali metal may be Na, K, or Li. Such a thickener may be included in an amount of about 0.1 parts by weight to about 3 parts by weight based on 100 parts by weight of the negative active material.

The conductive material improves conductivity of an electrode. Any electrically conductive material may be used as a conductive material, unless it causes a chemical change. Examples thereof may be a carbon-based material such as natural graphite, artificial graphite, carbon black, acetylene black, ketjen black, a carbon fiber, and the like; a metal-based material of metal powder or metal fiber including copper, nickel, aluminum, silver, and the like; a conductive polymer such as a polyphenylene derivative and the like; or a mixture thereof.

The positive electrode 114 includes a current collector and a positive active material layer formed on the current collector.

The current collector may be Al, but is not limited thereto.

The positive active material layer includes a positive active material, a binder, and optionally a conductive material.

The positive active material may include lithiated intercalation compounds that reversibly intercalate and deintercalate lithium ions. Specifically, at least one composite oxide of lithium and a metal of cobalt, manganese, nickel, or a combination thereof may be used, and specific examples thereof may be a compound represented by one of the following chemical formulae. $Li_aA_{1-b}R_bD_2$ (0.90≤a≤1.8 and 0≤b≤0.5); $Li_aE_{1-b}R_bO_{2-c}D_c$ (0.90≤a≤1.8, 0≤b≤0.5 and 0≤c≤0.05); $Li_aE_{2-b}R_bO_{4-c}D_c$ (0.90≤a≤1.8, 0≤b≤0.5, 0≤c≤0.05); $Li_aNi_{1-b-c}Co_bR_cD_\alpha$ (0.90≤a≤1.8, 0≤b≤0.5, 0≤c≤0.05 and 0≤α≤2); $Li_aNi_{1-b-c}Co_bR_cO_{2-\alpha}Z_\alpha$ (0.90≤a≤1.8, 0≤b≤0.5, 0≤c≤0.05 and 0≤α≤2); $Li_aNi_{1-b-c}Co_bR_cO_{2-\alpha}Z_2$ (0.90≤a≤1.8, 0≤b≤0.5, 0≤c≤0.05 and 0≤α≤2); $Li_aNi_{1-b-c}Mn_bR_cD_\alpha$ (0.90≤a≤1.8, 0≤b≤0.5, 0≤c≤0.05 and 0≤α≤2); $Li_aNi_{1-b-c}Mn_bR_cO_{2-\alpha}Z_\alpha$ (0.90≤a≤1.8, 0≤b≤0.5, 0≤c≤0.05 and 0≤α≤2); $Li_aNi_{1-b-c}Mn_bR_cO_{2-\alpha}Z_2$ (0.90≤a≤1.8, 0≤b≤0.5, 0≤c≤0.05 and 0≤α≤2); $Li_aN_{ib}E_cG_dO_2$ (0.90≤a≤1.8, 0≤b≤0.9, 0≤c≤0.5 and 0.001≤d≤0.1); $Li_aNi_bCo_cMn_dG_eO_2$ (0.90≤a≤1.8, 0≤b≤0.9, 0≤c≤0.5, 0≤d≤0.5 and 0.001≤e≤0.1); $Li_aNiG_bO_2$ (0.90≤a≤1.8 and 0.001≤b≤0.1); $Li_aCoG_bO_2$ (0.90≤a≤1.8 and 0.001≤b≤0.1); $Li_aMnG_bO_2$ (0.90≤a≤1.8 and 0.001≤b≤0.1); $Li_aMn_2G_bO_4$ (0.90≤a≤1.8 and 0.001≤b≤0.1); $QO_2$; $QS_2$; $LiQS_2$; $V_2O_5$; $LiV_2O_5$; $LiTO_2$; $LiNiVO_4$; $Li_{(3-f)}J_2(PO_4)_3$ (0≤f≤2); $Li_{(3-f)}Fe_2(PO_4)_3$ (0≤f≤2); and $LiFePO_4$.

In the above chemical formulae, A is Ni, Co, Mn, or a combination thereof; R is Al, Ni, Co, Mn, Cr, Fe, Mg, Sr, V, a rare earth element, or a combination thereof; D is O, F, S, P, or a combination thereof; E is Co, Mn, or a combination thereof; Z is F, S, P, or a combination thereof; G is Al, Cr, Mn, Fe, Mg, La, Ce, Sr, V, or a combination thereof; Q is Ti, Mo, Mn, or a combination thereof; T is Cr, V, Fe, Sc, Y, or a combination thereof; and J is V, Cr, Mn, Co, Ni, Cu, or a combination thereof.

The positive active material may include the positive active material with the coating layer, or a compound of the active material and the active material coated with the coating layer. The coating layer may include a coating element compound of an oxide of a coating element, hydroxide of a coating element, oxyhydroxide of a coating element, oxycarbonate of a coating element, or hydroxycarbonate of a coating element. The compound for the coating layer may be either amorphous or crystalline. The coating element included in the coating layer may be Mg, Al, Co, K, Na, Ca, Si, Ti, V, Sn, Ge, Ga, B, As, Zr, or a mixture thereof. The coating process may include any conventional processes as long as it does not causes any side effects on the properties of the positive active material (e.g., spray coating, immersing), which is well known to persons having ordinary skill in this art, so a detailed description thereof is omitted.

The binder improves binding properties of positive active material particles with one another and with a current collector. Examples thereof may be polyvinyl alcohol, carboxylmethyl cellulose, hydroxypropyl cellulose, diacetyl cellulose, polyvinylchloride, carboxylated polyvinylchloride, polyvinylfluoride, an ethylene oxide-containing polymer, polyvinylpyrrolidone, polyurethane, polytetrafluoroethylene, polyvinylidene fluoride, polyethylene, polypropylene, a styrene-butadiene rubber, an acrylated styrene-butadiene rubber, an epoxy resin, nylon, and the like, but are not limited thereto.

The conductive material improves conductivity of an electrode. Any electrically conductive material may be used as a conductive material, unless it causes a chemical change. Examples thereof may be one or more mixtures of natural graphite, artificial graphite, carbon black, acetylene black, ketjen black, a carbon fiber, a metal powder, a metal fiber and the like of copper, nickel, aluminum, silver, and the like, a conductive material of a polyphenylene derivative, and the like.

The negative electrode and the positive electrode may be manufactured by a method including mixing each active material, a binder, and a conductive material to provide an active material composition, and coating the active material composition on a current collector. The solvent may include N-methyl pyrrolidone and the like, but is not limited thereto. The electrode manufacturing method is well known, and thus is not described in detail in the present specification.

The separator 113 may include any materials commonly used in the conventional lithium battery as long as separating the negative electrode 112 from the positive electrode 114 and providing a transporting passage for lithium ions. In other words, the separator may have a low resistance to ion transportation and an excellent impregnation for an electrolyte. For example, it may be selected from glass fiber, polyester, TEFLON (tetrafluoroethylene), polyethylene, polypropylene, polytetrafluoroethylene (PTFE), or a combination thereof. It may have a form of a non-woven fabric or a woven fabric. For example, a polyolefin-based polymer separator such as polyethylene, polypropylene or the like is mainly used for a lithium ion battery. In order to ensure the heat resistance or mechanical strength, a coated separator including a ceramic component or a polymer material may be used. Selectively, it may have a mono-layered or multi-layered structure.

The rechargeable lithium battery may be classified into a lithium ion battery, a lithium ion polymer battery, and a lithium polymer battery depending on kinds of a separator and an electrolyte. It also may be classified to be cylindrical, prismatic, coin-type, pouch-type, and the like depending on shape. In addition, it may be bulk type and thin film type depending on size. Structures and manufacturing methods for the lithium batteries pertaining to this disclosure are well known in the art.

The electrolyte is the same as described above.

When the rechargeable lithium battery according to the present embodiments is operated in a high voltage region of greater than or equal to about 4.35V, cycle-life characteristics of a battery may be improved.

Hereinafter, the above aspects of the present disclosure are illustrated in more detail with reference to examples. However, the following are examples, and the present disclosure is not limited thereto.

Preparation of Electrolyte

Examples 1 to 4, Electrolytes of Comparative Example 1 and Reference Examples 1 to 3

An electrolyte was manufactured by mixing ethylene carbonate (EC), ethylmethyl carbonate (EMC), and dimethyl carbonate (DMC) in a ratio of 2/2/6 (v/v/v) to prepare a mixed solvent and adding 1.4 M $LiPF_6$ thereto and then, a compound represented by Chemical Formula 3 in a composition provided in the following Table 1.

TABLE 1

|  | Ethylene carbonate (volume %) | Ethylmethyl carbonate (volume %) | Dimethyl carbonate (volume %) | LiPF$_6$ (M) | Compound Represented by Chemical Formula 3 (parts by weight based on 100 parts by weight of the organic solvent) |
|---|---|---|---|---|---|
| Example 1 | 20 | 20 | 60 | 1.4 | 0.1 |
| Example 2 | 20 | 20 | 60 | 1.4 | 0.2 |
| Example 3 | 20 | 20 | 60 | 1.4 | 0.5 |
| Example 4 | 20 | 20 | 60 | 1.4 | 1.0 |
| Comparative Example 1 | 20 | 20 | 60 | 1.4 | — |
| Reference Example 1 | 20 | 20 | 60 | 1.4 | 2.0 |
| Reference Example 2 | 20 | 20 | 60 | 1.4 | 5.0 |
| Reference Example 3 | 20 | 20 | 60 | 1.4 | 10.0 |

Manufacture of Rechargeable Lithium Battery Cell

Examples 1 to 4, Comparative Example 1, and Reference Examples 1 to 3

A positive active material layer composition was prepared by mixing LiCoO$_2$, polyvinylidene fluoride (PVdF), and acetylene black in a weight ratio of 96:2:2 and dispersing the mixture into N-methyl-2-pyrrolidone. The positive active material layer composition was coated on a 20 μm-thick aluminum foil and then, drying and compressing it, manufacturing a positive electrode.

The positive electrode, a lithium metal counter electrode and a 25 μm-thick polyethylene separator were spirally-wound and compressed and then, inserted into a 18650 cylindrical (2800 mA) can, manufacturing a half-cell. Herein, the electrolytes according to Examples 1 to 4, Comparative Example 1, and Reference Examples 1 to 3 were respectively manufactured.

Evaluation: Electrolyte Decomposition Reaction Initiation Voltage

Figure 2:
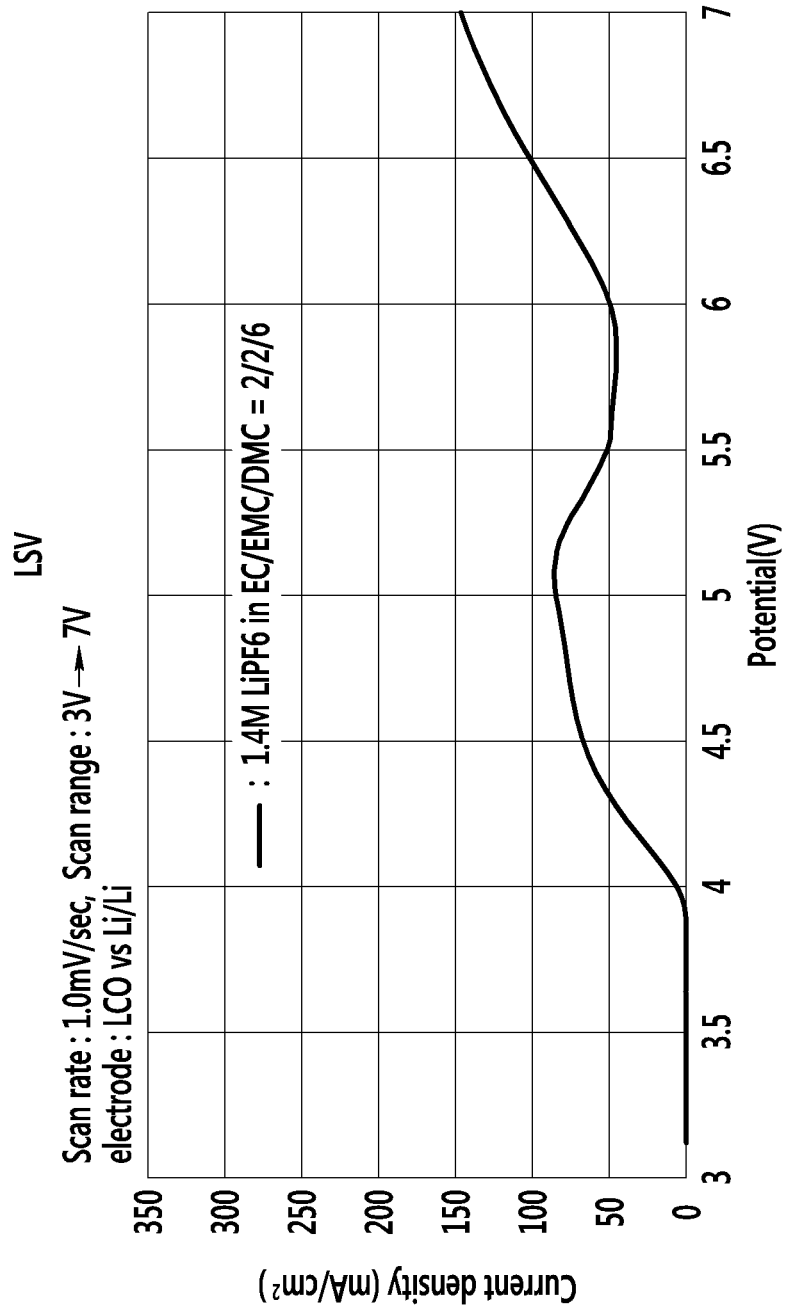
FIG. 2 is a LSV (Linear Sweep Voltammetry) graph showing a reaction initiation voltage of an electrolyte in a battery cell according to Comparative Example 1.
Figure 3:
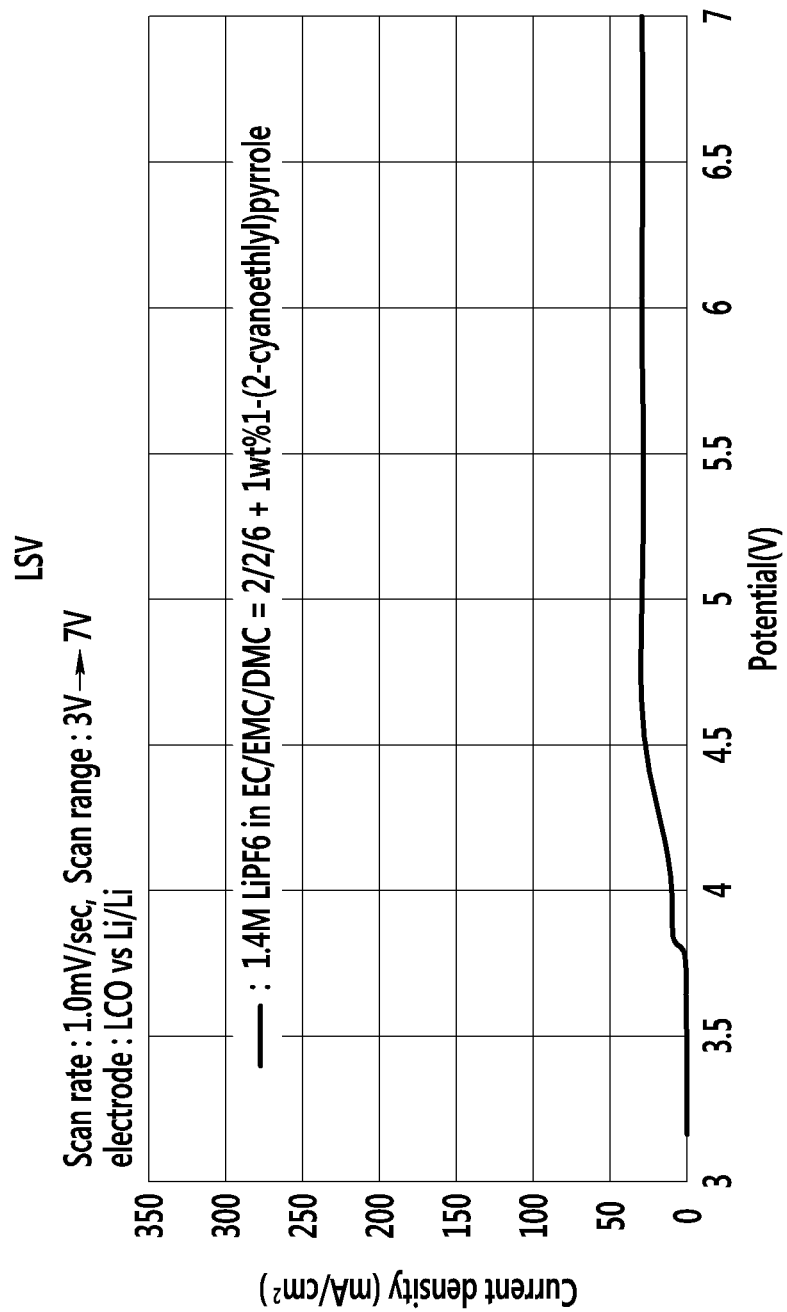
FIG. 3 is a LSV (Linear Sweep Voltammetry) graph showing a reaction initiation voltage of an electrolyte in a battery cell according to Example 4.

LSV (Linear Sweep Voltammetry) of each half-cell according to Examples 1 to 4, Comparative Example 1, Reference Examples 1 to 3 were measured at a scan rate of 1 mV/s was measured, and the results are provided in FIGS. 2 and 3.

The results are explained referring to FIGS. 2 to 5.

Figure 4:
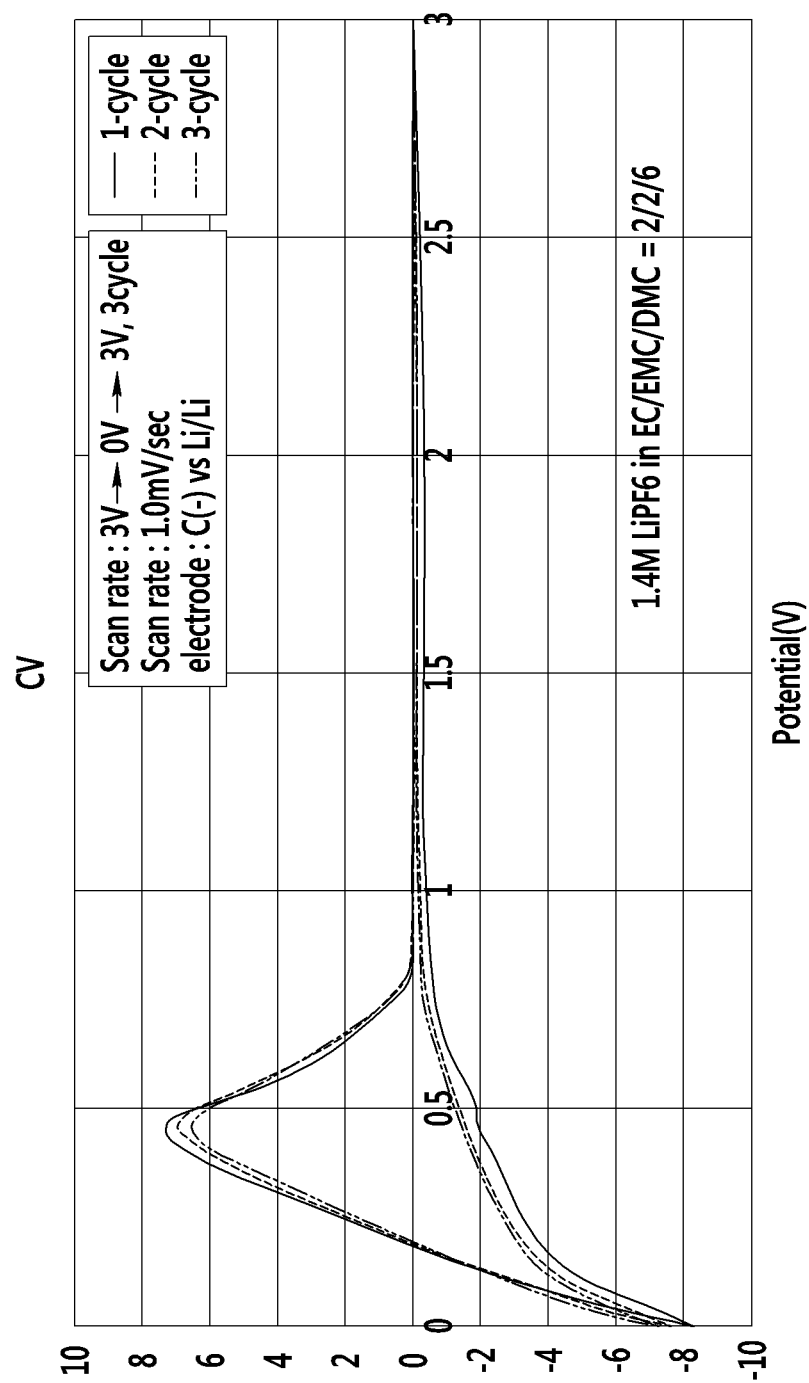
FIG. 4 is a graph showing CV (cyclic voltammetry) of the battery cell according to Comparative Example 1.
Figure 5:
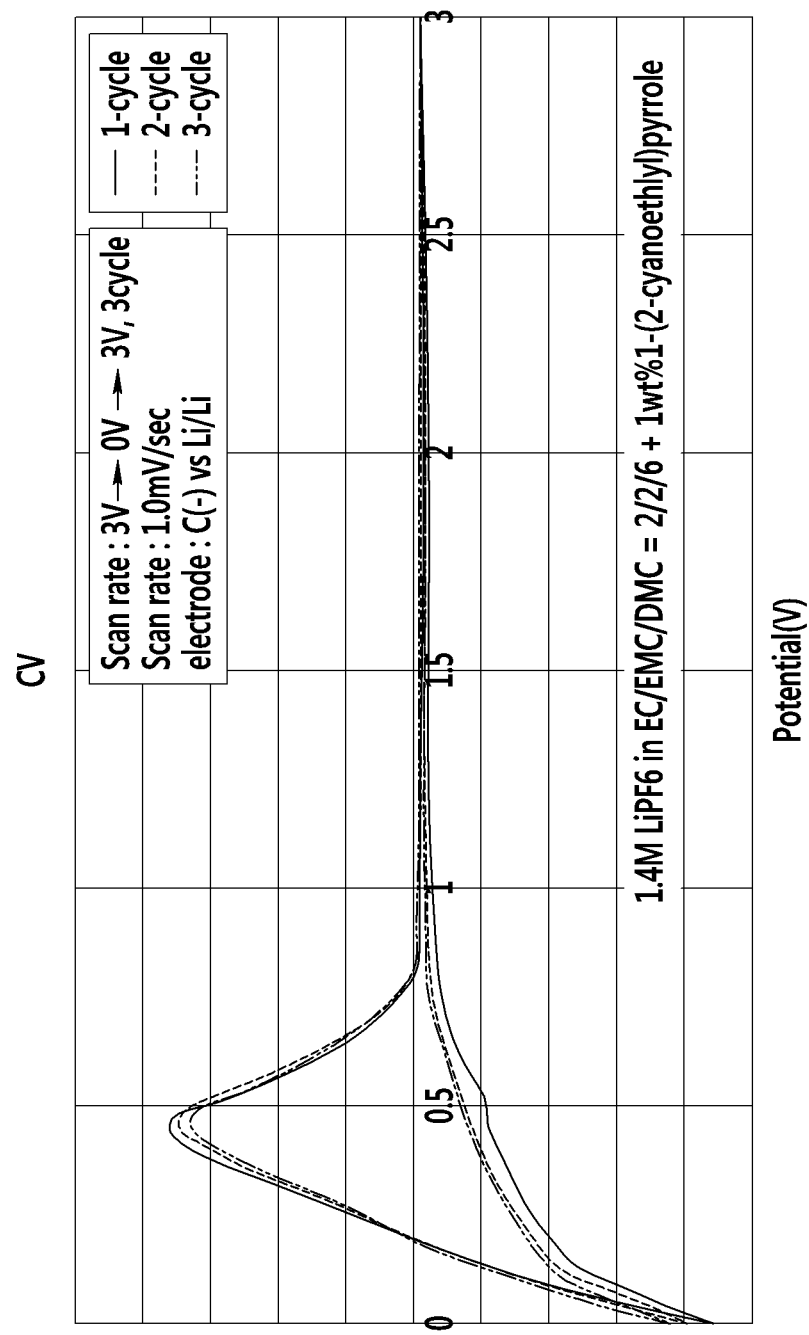
FIG. 5 is a graph showing CV (cyclic voltammetry) of the battery cell according to Example 4.

FIGS. 2 and 3 show LSV (Linear Sweep Voltammetry) obtained by measuring reaction initiation voltage of the electrolytes in the cells, and FIGS. 4 and 5 show CV (cyclic voltammetry) of the cells.

Referring to FIGS. 2 and 3, the electrolyte of Example 4 showed an oxidation-starting voltage of about 3.7 V, while the non-aqueous electrolyte of Comparative Example 1 showed an oxidation-starting voltage of about 3.9 V.

In, other words, the additive in the non-aqueous electrolyte of Example was oxidized and decomposed at a lower voltage than the oxidation-starting voltage of Comparative Example and thus, formed a passivation film on a positive electrode and had no influence on a negative electrode potential.

In addition, referring to FIGS. 4 and 5, the battery cell of Example 4 showed better reversibility and durability of oxidation/reduction reaction than the battery cell of Comparative Example 1.

Evaluation: Cycle-Life Characteristics

Cycle-life characteristics of the 18650 cells according to Examples 1 to 4, Comparative Example 1, and Reference Examples 1 to 3 were evaluated.

The cycle-life characteristics of the cylindrical 18650 cells of Examples 1 to 4, Comparative Example 1, and Reference Examples 1 to 3 were evaluated under the following condition.

1. Charge: CC/CV 1.0 C, 4.38V, 0.02 C Cut-off, Rest 10 min.
2. Discharge: CC 1.0 C 3V Cut-off, Rest 10 min.
3. Repeat greater than or equal to 300 cycles at 25° C.

Figure 6:
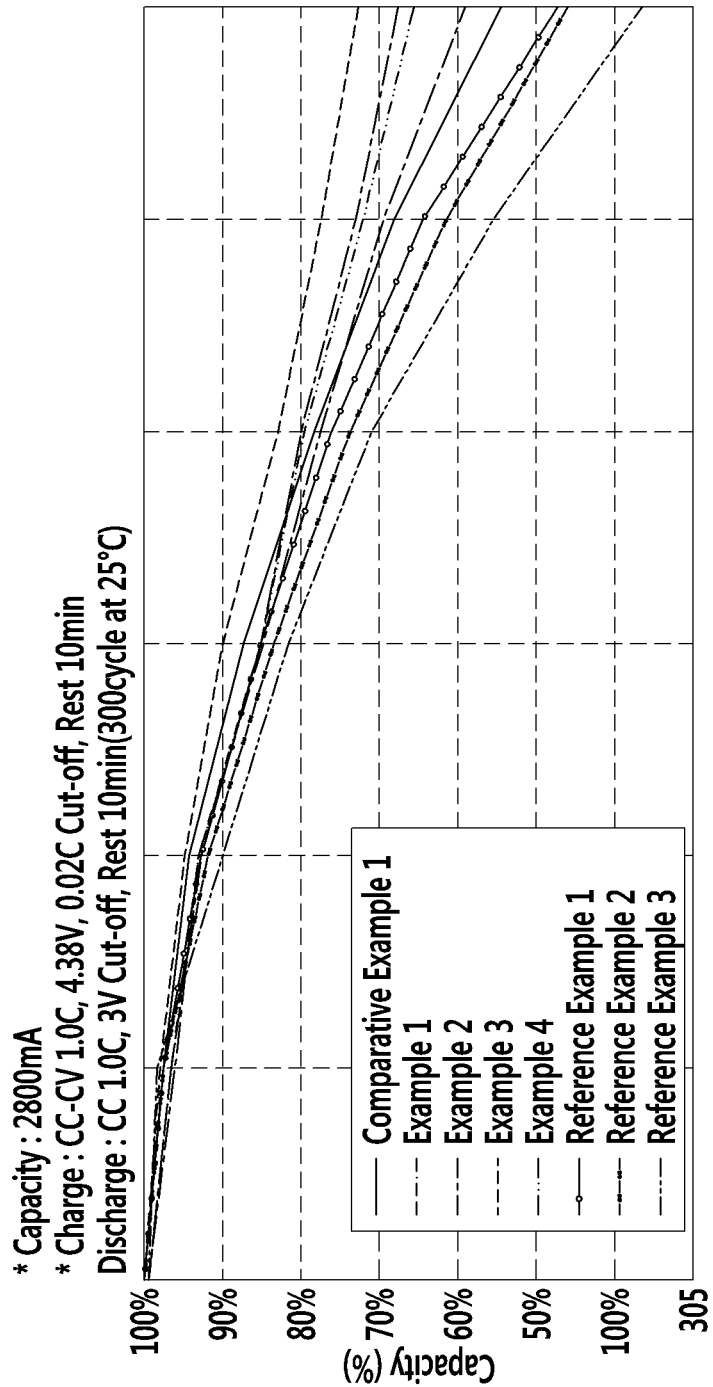
FIG. 6 is a graph showing capacity retention of the rechargeable lithium battery cells according to Examples 1 to 4, Comparative Example 1, and Reference Examples 1 to 3 depending on a cycle.

The results are provided in FIG. 6.

FIG. 6 is a graph showing capacity retention of the cylindrical 18650 cells of Examples 1 to 4, Comparative Example 1, and Reference Examples 1 to 3 depending on a cycle.

Referring to FIG. 6, the cylindrical 18650 cells of Examples 1 to 4 showed higher capacity retention than the cylindrical 18650 cells of Comparative Example 1 and Reference Examples 1 to 3 depending on a cycle.

While this disclosure has been described in connection with what is presently considered to be practical example embodiments, it is to be understood that the present embodiments are not limited to the disclosed embodiments, but, on the contrary, is intended to cover various modifications and equivalent arrangements included within the spirit and scope of the appended claims.

What is claimed is:

1. An additive for an electrolyte represented by the following Chemical Formula 1:

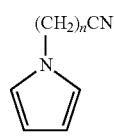

Chemical Formula 1 wherein n is an integer ranging from 1 to 3.

2. The additive for an electrolyte of claim 1, wherein Chemical Formula 1 is represented by the following Chemical Formula 3:

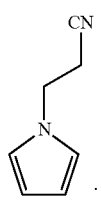

Chemical Formula 3

.

3. An electrolyte for a rechargeable lithium battery, comprising
a lithium salt;
a non-aqueous organic solvent; and
an additive for an electrolyte comprising a compound represented by the following Chemical Formula 1:

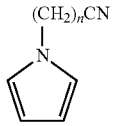

Chemical Formula 1 wherein n is an integer ranging from 1 to 3.

4. The electrolyte for a rechargeable lithium battery of claim 3, wherein Chemical Formula 1 is represented by the following Chemical Formula 3:

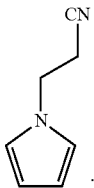

Chemical Formula 3

5. The electrolyte for a rechargeable lithium battery of claim 3, wherein the additive for an electrolyte is included in an amount of about 0.001 parts by weight to about 1 part by weight based on 100 parts by weight of the non-aqueous organic solvent.

6. The electrolyte for a rechargeable lithium battery of claim 3, wherein the additive for an electrolyte is included in an amount of about 0.1 parts by weight to about 1 parts by weight of the non-aqueous organic solvent.

7. A rechargeable lithium battery, comprising
a positive electrode including a positive active material;
a negative electrode including a negative active material; and
an electrolyte, comprising
a lithium salt;
a non-aqueous organic solvent; and
an additive comprising a compound represented by the following Chemical Formula 1:

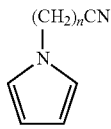

Chemical Formula 1 wherein n is an integer ranging from 1 to 3.

8. The rechargeable lithium battery of claim 7, wherein Chemical Formula 1 is represented by the following Chemical Formula 3:

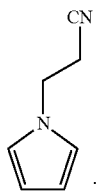

Chemical Formula 3

9. The rechargeable lithium battery of claim 7, wherein the additive for an electrolyte is included in an amount of about 0.001 parts by weight to about 1 part by weight based on 100 parts by weight of the non-aqueous organic solvent.

10. The rechargeable lithium battery of claim 9, wherein the additive for an electrolyte is included in an amount of about 0.1 parts by weight to about 1 part by weight based on 100 parts by weight of the non-aqueous organic solvent.

11. The rechargeable lithium battery of claim 7, wherein the positive electrode further comprises a passivation film disposed on the surface of the positive electrode.

12. The rechargeable lithium battery of claim 7, wherein the rechargeable lithium battery is operated at a voltage region of greater than or equal to about 4.35 V.

* * * * *

UNITED STATES PATENT AND TRADEMARK OFFICE
CERTIFICATE OF CORRECTION

PATENT NO. : 10,236,532 B2
APPLICATION NO. : 14/616598
DATED : March 19, 2019
INVENTOR(S) : Jin-Hyeok Lim Page 1 of 1

It is certified that error appears in the above-identified patent and that said Letters Patent is hereby corrected as shown below:

In the Specification

Column 5, Line 32, change "$(C_yF_{2y+1} SO_2),$" to --$(C_yF_{2y+1}SO_2)$,--.

In the Claims

Column 12, Line 46-50 (approx.), in Claim 1, after " 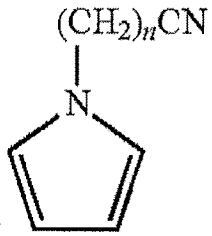 " insert --,--.

Column 13, Line 10-14 (approx.), in Claim 3, after " 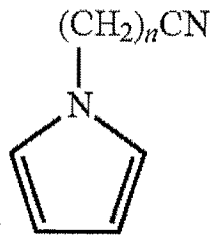 " insert --,--.

Column 14, Line 8-12 (approx.), in Claim 7, after " 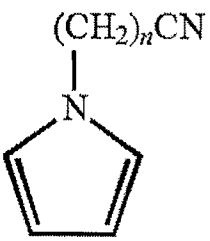 " insert --,--.

Signed and Sealed this
Ninth Day of July, 2019

Andrei Iancu
*Director of the United States Patent and Trademark Office*